United States Patent [19]

Touati et al.

[11] Patent Number: 4,764,118
[45] Date of Patent: Aug. 16, 1988

[54] FIXATION OF RIGID PIECES SUCH AS A DENTAL PROSTHESIS

[76] Inventors: Bernard Touati, 11, Place du Général Catroux, 75017 Paris; Marc Werly, 16 rue d'Odessa, 75014 Paris, both of France

[21] Appl. No.: 925,805
[22] PCT Filed: Feb. 27, 1986
[86] PCT No.: PCT/FR86/00065
§ 371 Date: Nov. 12, 1986
§ 102(e) Date: Nov. 12, 1986
[87] PCT Pub. No.: WO86/05085
PCT Pub. Date: Sep. 12, 1986

[30] Foreign Application Priority Data

Feb. 28, 1985 [FR] France ................................ 85 02920

[51] Int. Cl.⁴ .............................................. A61C 5/04
[52] U.S. Cl. ............................. 433/226; 433/228.1; 433/229; 156/272.2
[58] Field of Search ................ 433/180, 191, 192, 204, 433/205, 223, 226, 228, 183, 9, 229; 156/272.2, 314, 332

[56] References Cited

U.S. PATENT DOCUMENTS 3,423,829 1/1969 Halpern et al. ...................... 433/191
4,272,589 6/1981 Dubois et al. ....................... 428/442

Primary Examiner—John J. Wilson
Attorney, Agent, or Firm—Fisher, Christen & Sabol

[57] ABSTRACT

The present invention relates to the positioning and fixation by gluing of pieces.

According to the invention, the piece adapted to be connected to a support, for example a prosthesis, particularly dental prosthesis (3), comprises an opaque region (7) associated with a rear translucent region (8) and corresponding to that part coming opposite the receiving support wall; the gluing interface (12) is constituted by a photopolymerizable resin; an optical fiber (9) passing through the opaque region (7) makes it possible to illuminate the interface (12) through the translucent part (8), ensuring photopolymerization of the adhesion resin constituting the interface and to ensure gluing of the two pieces.

8 Claims, 1 Drawing Sheet

FIXATION OF RIGID PIECES SUCH AS A DENTAL PROSTHESIS

The present invention relates to the positioning and fixation of pieces added on a support.

More especially, the invention relates to the positioning and fixation of prostheses constituted by a rigid element added and connected on a support which is itself rigid, such as a tooth or an osseous member.

The invention relates more particularly to the connection of dental prostheses such as an inlay intended to fill in a cavity or to complete a missing part of the tooth further to the development of dental decay or to accidental breaking thereof.

The invention may generally be applied to all operations aiming at ensuring connection of a rigid piece or block intended to be added on a rigid support; however, the invention will be described hereinafter more especially in its preferred application which concerns the positioning of prostheses, particularly in the domain of dental surgery.

The repair of the dental apparatus, particularly at the level of a tooth degraded by decay or of which the entirety has been modified or attacked accidentally, aims at reconstituting the profile and shape of the tooth, so as to allow the latter to perform its role in the buccal and dental assembly, ensuring the optimum conditions of physical and biological stability for the structure thus reconstituted.

The practician conventionally treats slight, superficial attacks by a mechanical cleaning of the gap constituted in the structure of the tooth, creating a cavity of which the walls rendered healthier may receive a filling material generally positioned by moulding.

In this case, the joining of the material (amalgam or cement) is obtained by crimping the material in the cavity of which the edges are narrow or by micro-keying of the stopping material in the micro-retentions created on the surface of the walls of the cavity to be stopped.

These conditions define the limits of the domain of application of these conventional techniques; in particular when the size of the missing part to be replaced does not make it possible to constitute a cavity with narrow edges allowing a crimping effect.

In the latter case, it is then necessary to make a prosthesis representing the missing part of the tooth which must be positioned and joined exactly on the healthy part to ensure for the whole the shape and contour of the reconstituted tooth.

This prosthesis or inlay (pre-fabricated in the workshop in conventional manner and from an impression of the jaw object of the treatment) must therefore be connected to the remaining part of the tooth and which was previously rendered healthier so as to reconstitute the tooth in its operational form.

Connection of the dental prosthesis, particularly constituted by an inlay, is obtained by gluing by means of an appropriate bonding agent or adhesive and among which various resins are used.

Polymerization of the resin in situ constitutes the interface ensuring connection between the wall of the cavity and the wall coming into register and of profile complementary of the prosthesis.

Initiation of the reaction of polymerization which will allow the hardening of the bonding agent and connection of the prosthesis in its receiving location is generally obtained chemically.

This means that the resin which constitutes the adhesive is therefore mixed immediately before its use with a second component comprising a catalyst of polymerization and constituting the hardener.

The use of this method of chemical gluing supposes the carrying out of prior operational phases aiming at giving the wall of the receiving cavity an appropriate surface state allowing a maximum spread and consequently an efficient adherence of the bonding agent on this wall, in order to obtain both a good cohesive bond (between the adhesive and the support material) and a good adhesive bond (within the adhesive material itself).

Presently used adhesive resins with polymerization by the chemical process give cohesions which are satisfactory on the whole but which create delicate problems when employed.

These problems are caused by the fact that it is by definition necessary to initiate the reaction of polymerization before the adhesive and the prosthesis are positioned.

And the reaction of polymerization must necesarily be included within a relatively short lapse of time in order to render this operation supportable by the patient.

It follows that the practician has only a very limited time at his disposal to ensure correct adjustment of the prosthesis; and if corrections or a more precise adjustment appear necessary, the practician finds it impossible to effect it comfortably as the whole is rapidly immobilized.

Another drawback comes from the fact that the excess of adhesive which overflows at the join between the prosthesis and the edges of the healthy part of the tooth, also solidifies in situ and the operation of correction of the ball of the tooth at this level, so as to recover a continuous wall by "fettling" the projecting parts of adhesives, are difficult and delicate to carry out.

In fact, if the practician proceeds with the removal of the projecting excess adhesive before polymerization and before solidification, he risks affecting the correct positioning of the prosthesis and moving it inadvertently.

And if the practician, in order to avoid this drawback, waits for firm and definitive connection of the prosthesis, he is then faced with an excess of adhesive which, by definition, is very solid and which will therefore require considerable work of the tool in order to arrive at a perfect surfacing and continuity of the wall all along the join between the prosthesis and dental support.

It has therefore appeared desirable to have available an adhesive capable of being positioned in the liquid state both on the wall of the receiving dental structure and on the wall of the prosthesis coming opposite, the resin remaining in its liquid state without polymerization for the time necessary for the useful adjustment and verifications allowing a correct final positioning of the prosthesis, then to initiate the polymerization reaction upon outside control and when the practician considers that the correct positioning is obtained and that the assembly can then be set in the position that he has ensured; somewhat like the photographer who effects adjustment of his camera on his focussing screen before taking the photograph on the sensitive plate when he has ensured that the conditions of the successful image are combined.

Resins are doubtlessly known whose polymerization reaction may be initiated from outside by an electromagnetic radiation, particularly in the wave-lengths corresponding to visible light, with the result that these resins may be positioned and deposited in situ in the liquid state, possibly worked in the liquid state, without the polymerization reaction being triggered, these resins polymerizing upon reception of a radiation in an appropriate wave-length; consequently it is possible to initiate the polymerization reaction at the desired moment by directing on the layer of resin in place the radiation in the desired wave length.

Furthermore, these photo-polymerizable resins are used in dental practice and in odontological surgery; they serve in particular for the reconstitution of the dental wall by stopping cavities or irregularities in relief of reduced dimensions, and for which it is possible to stop the receiving cavity by a layer of resin on one occasion.

When the cavity exceeds a certain dimension, it then becomes necessary to operate in several layers deposited successively, this already leading to rendering the operation complex and raising the problem of cohesion of the successive layers to one another so that the treatment of stopping and of reconstitution of the dental wall by photo-polymerizable resin lies in a relatively narrow range of application.

In particular, the use of photo-polymerizable resins has not been able to be carried out within the framework of the positioning and joining of prostheses constituted by rigid blocks or inlays added on a dental support structure.

In fact, it will be understood that the reaction of initiation of polymerization, triggered off by the light irradiation, supposes that the layer of resin is accessible to said radiations from the outside.

Now, precisely in the case of positioning a prosthesis, particularly an inlay, the adhesive constitutes an interface between the support wall of the tooth and the wall of the prosthesis coming opposite, interface whose thickness is necessarily very limited and this interface is therefore not accessible to the light radiations capable of catalyzing the reaction of polymerization.

Now, it is obvious that it is especially in the case of positioning a prosthesis that the possibility is sought of an adhesive allowing, after application, the works of adjustment and of verification before triggering off the polymerization which will definitively set the prosthesis in place.

The invention overcomes these drawbacks and precisely allows the fixation of a piece such as a prosthesis on a support, particularly a dental support, by means of a photopolymerizable resin.

To this end, the invention relates in the first place to a piece or component of the type constituted by a rigid block adapted to be added and joined, by seal or gluing, on a support, itself rigid, such as a prosthesis or an inlay intended to stop a cavity in said rigid support, characterized in that the block comprises at least two regions, viz. one opaque region defining a facade appearing on the outside and a translucent region oriented towards the wall of the support and adapted to constitute a zone of diffusion of radiations, particularly light radiations, in order to initiate the reaction of polymerization of a photopolymerizable resin constituting the interface of seal or gluing between the receiving wall of the support and the opposite wall of the added block.

And, preferably, said opaque region is traversed by a passage opening out on one side towards the outside medium through the facade of this opaque region and opening out on the other side in said translucent region, this passage allowing the guiding of the radiations, particularly of light, from the outside up to in said translucent region, in order to initiate the reaction of photopolymerization of said resin constituting the interface of seal or of gluing.

For example, said passage constituting channel for guiding the light waves catalyzing the reaction of polymerization is constituted by the same material as the translucent part of the prosthesis.

According to a more particular embodiment said passage is occupied by an optical fiber arriving by one end in said translucent region of the prosthesis.

And more particularly, the optical fiber is provided to project outside said opaque region to allow the exposure of its free end to the emission of a source of light radiation such as a laser ray.

It will be understood that the piece, particularly the prosthesis thus made, enables the practician to ensure the positioning of the gluing resin of the photopolymerizable type which remains in its liquid state without any phenomenon of hardening for all the necessary time during which the practician can carry out the useful corrections, adjustments and verifications; and the reaction of polymerization may then be triggered off from the outside by light irradiation, the radiations passing through the opaque part of the prosthesis and spreading and diffusing to the rear thereof, in the interface occupied precisely by the photopolymerizable resin, the light being spread by the rear translucent part of the prosthesis.

According to one development of the invention, the prosthesis is characterized in that, in the translucent region, there is provided a means of diffraction of the light radiations, such as a prism, this latter being located at the opening of said passage in particular at the opening of the optical fiber in the translucent region, this means of diffraction ensuring the distribution of the radiations over the whole of the interface between the prosthesis and the wall of the receiving cavity.

According to a more particular embodiment, the two opaque and translucent regions respectively of the prosthesis are made of a resin of the same nature, the opaque region being constituted by a resin identical to the resin of the translucent region and comprising fillers of appropriate density and granulometry and adapted to give this opaque part a suitable coloration.

It will be understood that the use of the same resin to constitute the block forming the prosthesis makes it possible to ensure perfect conditions of homogeneity of said block, the opaque part, having to constitute the facade of the prosthesis differing from the translucent rear part by the presence of fillers, particularly pigmentary fillers of mineral nature, of appropriate density greater in the vicinity of the outer wall constituting the visible facade of the prosthesis.

According to another feature corresponding to an embodiment of the invention, the block of resin is constituted by a single resin defining the two opaque and translucent regions respectively, and itself formed by a single resin of the photopolymerizable type and of which the reaction of polymerization has been initiated by irradiation of a light radiation of a determined wavelength.

To this end, the invention further relates to a process for making a prosthesis, characterized in that a first layer of translucent resin constituting the inner translucent region is cast into a hollow impression of appropriate shape, onto which first layer is cast a second layer of resin laden with pigmentary particles in order to constitute the opaque region of said prosthesis.

And according to a form of embodiment of this process, prior to the casting of the second layer of laden resin, the end of an optical fiber is brought into position in contact with the layer of translucent resin and the laden resin intended to constitute the opaque region of the prosthesis is cast around said fiber thus embedded in the opaque region of the prosthesis that it traverses, the free end of the fiber projecting outside in order to allow exposure thereof to the light radiations.

The invention also relates to the implementation of a prosthesis such as defined previously and such implementation is characterized in that the prosthesis is inserted in the receiving cavity such as a dental or osseous cavity, after interposition on the wall of the cavity and/or on that part of the wall of the prosthesis located opposite, of an interface of gluing or seal constituted by a photopolymerizable resin in the liquid state, and after adjustment and verification of the positioning of the prosthesis, the photopolymerizable resin constituting the interface adhesive between the wall of the receiving cavity and of the prosthesis is exposed to the irradiation of a radiation of wave-length specific to said resin and adapted to initiate the reaction of polymerization, said radiation being guided from an outside source by means of the optical fiber embedded in said prosthesis.

And according to another feature, that part of the optical fiber projecting outside is then cut off flush with the visible facade of the prosthesis.

The invention also relates to an irradiation apparatus for making a prosthesis as defined hereinabove and associated with an adhesive positioned in interface between the prosthesis and the wall of the receiving cavity and constituted by a photopolymerizable resin, the apparatus being characterized in that it is constituted by a source of laser radiations of the argon laser type adapted to transmit by the optical fiber associated with the prosthesis and of which the free end is previously disposed opposite the source of the emission, a light irradiation catalyzing the reaction of polymerization of the sealing resin.

Other characteristics and advantages of the invention will appear from the following description which is given in connection with a particular embodiment presented by way of non-limiting examples with reference to the accompanying drawings.

Figure 1:
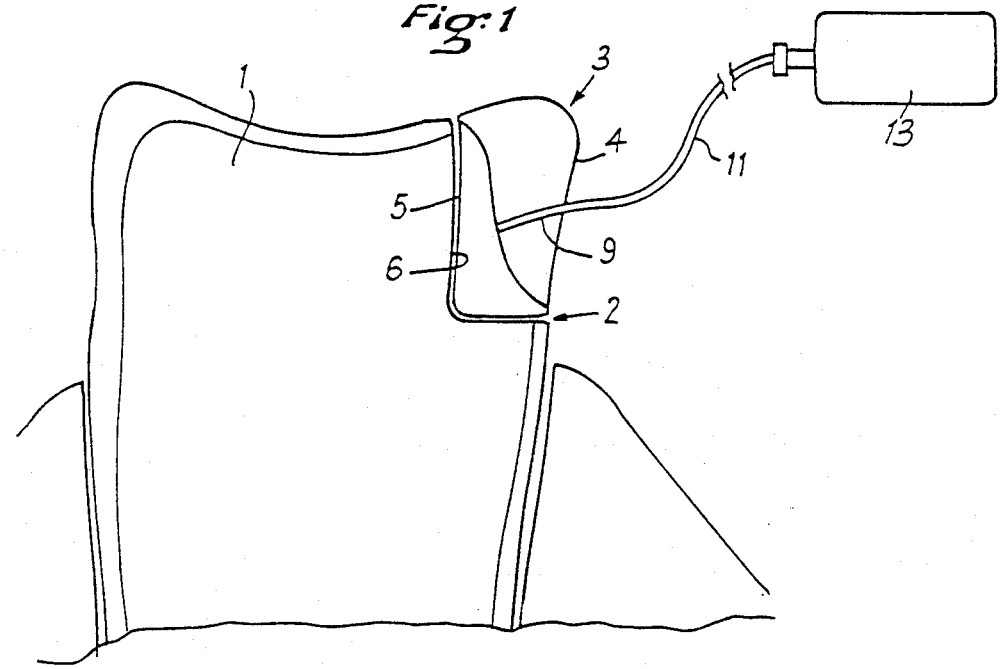
FIG. 1 shows a view in section of a tooth comprising a prosthesis according to the invention in the course of joining.

The example described here is (sic) shown in the drawings, relates to the positioning of an inlay replacing the missing part of a tooth.

The support tooth 1 therefore presents a cavity 2 in which will be positioned the prosthesis or inlay 3 provided with an outer wall 4 of which the contour is provided to extend and reconstitute the outer wall of the missing part of the tooth whilst an inner wall 5 is positioned opposite the inner wall 6 of the cavity 2 in which it is fitted, being provided with an exactly complementary shape.

The invention makes it possible to ensure, under clearly improved conditions, the connection of the prosthesis 3 in its receiving housing 2.

According to the invention, the prosthesis constituted by a block of resin comprises two parts, viz. a so-called outer part 7 of which the wall 4 corresponds to the facade of the prosthesis oriented outwardly and extending the outer wall of the tooth.

And the prosthesis comprises an inner part 8 of which the wall 5 comes opposite, with a complementary profile, the wall 6 of the receiving housing 2.

And according to the invention, whilst the so-called outer part 7 is provided to be opaque and more especially white, the inner part 8 is provided to be translucent.

To that end, according to an embodiment, the two parts composing the prosthesis 3 may be made in one and the same material, for example a synthetic resin such as a methacrylate.

Whilst the inner part 8 is constituted by pure or substantially pure resin, consequently forming a translucent and transparent volume, the so-called outer part 7 is constituted by the same resin but comprising pigmentary mineral fillers giving this outer part a milky white aspect and provided to be of the same colour as the part of the support tooth 1, with the result that, when the prosthesis is in position, it merges with the outer surface of the whole of the tooth.

And according to the invention, the translucent part 8 is in communication with the outside via a channel traversing the opaque part 7.

The channel, of very fine dimensions, particularly of capillary dimensions, may be constituted by the same material as part 8, i.e. of pure, non-laden translucent resin.

Figure 2:
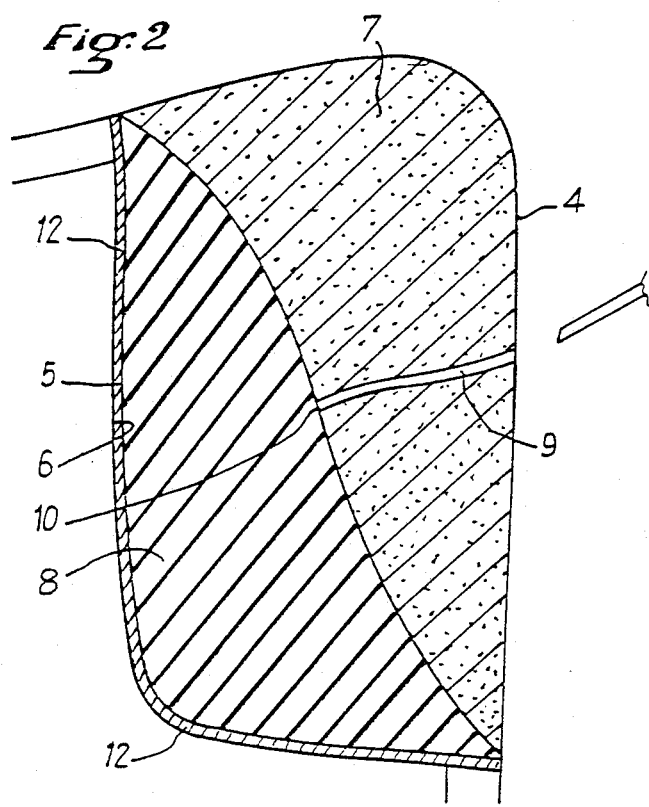
FIG. 2 shows an enlarged view in section of the prosthesis of FIG. 1.

According to the variant which is shown in FIGS. 1 and 2, the channel is occupied by an optical fiber 9 which passes through the opaque part 7 of the prosthesis.

This optical fiber 9 opens out by one end 10 in the translucent part 8 of the prosthesis; and in particular the terminal end 10 may be embedded inside this translucent part; the fiber 9 projects on the opposite side beyond the wall 4 of the opaque part of the prosthesis and extends outwardly.

The implementation of the prosthesis according to the invention will illustrate the interest and advantages thereof.

After the prosthesis 3 has been offered in its receiving housing to verify the general adjustment of the two complementary walls, one or preferably both opposite walls 5 and 6 respectively are coated with a layer of an adhesive constituted according to the invention by a photopolymerizable resin.

Acrylic resins will advantageously be used, particularly the micro-laden resins based on methacrylates such as the products known under the trademarks Silux, Heliosit, Prismafill, Dentacolor, etc . . .

These resins in the non-polymerized state are presented in a viscosity allowing a good wettability of the walls, factor of a satisfactory subsequent adherence.

The practician may then reposition the prosthesis in its receiving housing and proceed with the necessary ultimate adjustments or verifications, the prosthesis then being in situation since it already comprises its adhesion interface constituted by the layer of photo-sensitive resin 12.

In fact, this resin will remain in its state of initial viscosity consequently allowing all useful verifications, adjustments and repositions without the polymerization reaction being triggered off whereas, in the framework of the use of resin with polymerization initiated chemically, the adhesion resin is positioned whilst the process of polymerization has already started and consequently hardening occurs, limiting and finally preventing any possibilities of correction or work of the practician.

In the implementation of the present invention, the practician therefore has all the necessary time at his disposal for verifying all the parameters making it possible to result in a correct operation.

In particular, the practician has at his disposal all the time necessary for removing the burrs or excesses of adhesion resin which may project at the level of the join between the prosthesis and the healthy part of the support tooth; and this whilst respecting and then verifying the correct positioning of the prosthesis.

When all the adjustments have been made under perfect conditions of comfort and safety, and when the final positioning of the prosthesis is correct with respect to the receiving housing, the excesses of adhesives having been cleaned, the practician may then trigger off the reaction of polymerization which will almost instantaneously crystallize the positioning of the prosthesis, ensuring connection thereof with respect to the support tooth.

To this end, the end 11 of the fiber 9 which projects to the outside may be brought opposite a light source, for example a laser 13.

To this end, the photo-polymerizable resin and the emitter apparatus 13 of the laser type will have been chosen in concordance with respect to each other so that the photopolymerizable resin positioned in the interface 12 is sensitive to the light radiation emitted by apparatus 13.

An insolation from the emission apparatus 13 is transmitted by the wave guide constituted by the optical fiber 11 up to the level of the translucent part of the prosthesis 8 in which the light rays are diffused being received by the interface 12 occupied by the photopolymerizable resin.

Consequently, this interface of resin 12 receives the light radiations over the whole of its extent, from wall 5 of the translucent part of the prosthesis, thus triggering off the reaction of polymerization of the resin.

And in this way the practician may, from the outside and at the desired moment, ensure instantaneously the definitive fixation of the prosthesis in the position which was previously verified and defined.

The photopolymerizable resins used for connecting the prosthesis are known per se.

And they comprise a mineral filler based in particular on silicon dioxide, alumina silicate or lithium silicate, allowing correct coloration thereof; with the result that the join constituted by the interface 12 between the support tooth constituted and the prosthesis, which opens out over a small thickness at the level of the outer surface, is itself of coloration in harmony with the rest of the tooth and the prosthesis appears to the eye to merge.

However, whilst so-called "composite" resins with light-initiated polymerization have hitherto been used only for very localized work, in which the composite resin itself reconstituted the missing wall of the tooth, within the framework of the present invention, the composite resin with polymerization by light is used as adhesive in the interface of a prosthesis and the support housing, in an invisible part, polymerization being initiated by an outside catalyst.

And this clearly distinguishes the application of the photosensitive composite resins within the framework of the present invention with respect to the prior art; in fact, in the prior art, the application of these resins was limited to the case of the irradiation of the resin being obtained directly from the outside; whereas within the framework of the present invention, irradiation of the layer of photosensitive resin serving as adhesive is obtained whilst this layer of photopolymerizable resin is hidden and consequently normally inaccessible for the catalytic initiation by light.

It will be understood that it is easy, the polymerization operation and connection of the prosthesis being effected, to cut the fiber 9 as shown in FIG. 2, flush with the outer wall 4 of the prosthesis.

However, in another variant, the prosthesis may be provided with a fiber or a channel constituting light wave guide 9 flush with the level of the surface 4 and irradiation is then obtained by bringing the light emission apparatus 13 opposite and at the level of the opening of the fiber 9 with respect to wall 4.

And this may also be used in the case of the channel which passes through the opaque part of the prosthesis being occupied not by a fiber 9 but by a filament of resin extending the resin of the translucent part 8.

The invention is also applied to the production of a prosthesis as described hereinabove; from a hollow impression corresponding to the impression of the receiving housing 2, a first layer of pure or translucent resin corresponding to layer 8 may be cast; and the fiber 9 may then be positioned, its end 10 opening out in the translucent part 8 whilst being embedded on the upper surface of this translucent region 8; following which the opaque region 7 is cast in particular from a resin identical to that constituting the translucent region 8, this resin then comprising pigmentary particles with a view to ensuring the appropriate coloration of the outer facade 4; in this operation, fiber 9 is embedded within the opaque region 7 whilst it projects by its part 11 to allow exposure of its terminal part 14 in front of the source of laser radiation 13.

In the case of application of the invention to the positioning of a prosthesis, particularly a dental prosthesis, the light irradiation of the photopolymerizable interface being effected from the centre, the practician may easily verify the efficiency of the operation of connection.

In fact, it is possible to ascertain at the level of the join between the prosthesis and the dental support, the production of polymerization of the resin interface by verifying the state of solidification of this interface at the level of the relatively accessible edges.

And this ascertainment is sufficient to make it possible to deduce that the connection is effective over all the interface; in fact, since the operation of photocatalytic initiation started from the central zone (which is the closest and located in line with the opening of the wave guide 10, the polymerization which started from the centre spreads by degrees up to towards the periphery.

And when polymerization is ascertained at the level of the periphery, it may therefore be deduced that it is for greater reason effective and operational in the invisible and inaccessible central zone.

Consequently, in addition to the convenience of operational implementation obtained within the framework of the invention, security in the verification of the result may also be obtained.

As has been specified, although the invention has been more especially described in connection with the operation for positioning a prosthesis and in particular a dental prosthesis, the application of the principle of the invention may be extended to the connection of a piece on any support, this in all domains whether it is question of operation of connection by craftsman or industrial manufacture in which component elements are added to a support for example within the framework of the production of an electronic assembly from component elements; in numerous cases where the strictly exact matching of the piece or of the component with respect to its support must be verified, it is then desirable to avoid using gluing by resin with polymerization initiated chemically which presents the drawbacks set forth previously, namely the necessity of starting the reaction of polymerization before assembly with the result that the verification time is reduced.

On the contrary, within the framework of the embodiment of the invention, it is possible to ensure connection of a piece or a component on a support by using photosensitive resins, even when these latter are intended to ensure connection by an interface normally non-accessible to a light irradiation.

The use of photosensitive resin thus makes it possible, as has been seen, to ensure the positioning of the gluing resin whilst then allowing, for an undefined and possibly extended time, the operations of matching and adjustment of the positioning; and when such adjustment is then verified, it is possible without any physical contact with the piece, to trigger off the operation of connection of the gluing interface by sending, via a wave guide fiber opening outside and passing through the opaque face of the piece up to a rear translucent region, a light emission irradiating, through the translucent part of the piece, the interface of photopolymerizable resin which is thus rigidified, ensuring connection of the two elements, in the correct position which was verified previously

We claim:

1. Process for connecting by gluing a piece constituted by a rigid block on a support to stop a cavity in said support, such as a prosthesis intended to fill a tooth cavity, said process comprising the following steps of:
    casting a hollow impression of said cavity;
    forming, by casting in said hollow impression, a first layer of a resin to constitute an inner region of said piece;
    forming a second layer of resin laden with pigmentary particles which is cast in said hollow impression and over said first layer to shape the outer part of the said piece;
    interposing on the wall of said cavity or on the wall of said piece a gluing interface constituted by a polymerizable resin in the liquid state;
    inserting said piece in said receiving cavity, the polymerizable resin constituting an interface between the walls of said receiving cavity and of said piece;
    adjusting said piece in said receiving cavity so as to ensure correct positioning thereof and removing the excess of polymerizable liquid resin likely to protrude outside of said piece and support;
wherein
    (a) said first layer is made from a translucent resin,
    (b) said second layer is cast as to leave a passage inside said second layer which passage opens on one side in said first layer of translucent resin and opens on the other side on the outside of said second layer,
    (c) the resin in the liquid state forming the gluing interface between the walls of said receiving cavity and said piece is photopolymerizable,
    (d) after the stage of enduring the correct positioning of the piece an insolation is directed from an external source through said passage, said insolation being of wave length specific of said photopolymerizable resin and adapted to initiate the reaction of polymerization, so that the irradiation is guided from the outside source up to said first layer of translucent resin which is thus able to spread said radiation onto said interface of photopolymerizable resin.

2. The process according to claim 1 wherein the step of leaving a passage in said second layer is performed by positioning an optical fiber in contact with the layer of translucent resin and the laden resin intended to constitute the said second layer of the piece is cast around said fiber which is embedded in the second and opaque layer of the piece that it traverses, the free end of the fiber projecting to the outside in order to allow exposure thereof to the said radiation, and wherein, after said insolation and polymerization of the photopolymerizable resin, that part of the optical fiber projecting to the outside is cut flush with the outer face of the said piece.

3. Piece of the type constituted by a rigid block adapted to be connected by a process of gluing on a rigid support, such as a prosthesis or an inlay intended to stop a cavity in said rigid support such as a tooth, the process of gluing comprising the steps of interposing between the walls of the cavity and the wall of the piece an interface of photopolymerizable resin and subsequently directing from an external source an insolation of radiation adapted to initiate the reaction of polymerizable of the resin, wherein the block comprises a first layer forming a translucent region oriented towards the wall of the support and adapted to constitute a zone of diffusion of radiation to initiate the reaction of polymerization resin constituting a gluing interface and said block comprises a second opaque layer integral with said first layer and defining the outer facade of said piece and said second and opaque layer is provided with a passage opening on one hand towards the outer face of said second layer and on the other side opening in said translucent layer, this passage allowing the guiding of said radiations from the external source to said first translucent layer.

4. The piece according to claim 3 wherein said passage allowing the guiding of radiations up to the first translucent layer is constituted by the same material as the translucent part of the piece.

5. The piece according to claim 3 wherein the said passage is constituted by an optical fiber terminating at one end in said translucent layer of the piece and said optical fiber projects outwardly in order to allow exposure of its free end to the emission of a source of radiation.

6. Piece according to claim 5 wherein said optical fiber is provided projecting to the outside of said opaque region to make possible the exposure of its free end to the emission of a luminous radiation source such as a laser emitter.

7. Piece according to claim 6 wherein said translucent region is provided a means for diffraction of the luminous radiations, such as a prism, this latter being located at the mouth of said passage, particularly at the mouth of said optical fiber in the translucent region, this diffraction means assuring the distribution of the radiations over the entire interface between the prosthesis and the wall of the receiving cavity.

8. Piece according to claim 7, wherein the two regions respectively opaque and translucent of the prosthesis are made of a resin of the same nature, the opaque region consisting of a resin identical with the resin of the translucent region and comprising charges in density and appropriate granulometry and able to give this opaque part a suitable coloring.

* * * * *